US006271021B1

(12) United States Patent
Burns et al.

(10) Patent No.: US 6,271,021 B1
(45) Date of Patent: Aug. 7, 2001

(54) MICROSCALE DEVICES AND REACTIONS IN MICROSCALE DEVICES

(75) Inventors: Mark A. Burns; Carlos H. Mastrangelo; Timothy S. Sammarco; Francis P. Man; James R. Webster; Brian N. Johnson; Bradley Foerster; Darren Jones, all of Ann Arbor, MI (US)

(73) Assignee: The Regents of The University of Michigan, Ann Arbor, MI (US)

( * ) Notice: Subject to any disclaimer, the term of this patent is extended or adjusted under 35 U.S.C. 154(b) by 0 days.

(21) Appl. No.: 09/271,963

(22) Filed: Mar. 18, 1999

Related U.S. Application Data

(62) Division of application No. 08/529,293, filed on Sep. 15, 1995, now Pat. No. 6,057,149.

(51) Int. Cl.[7] .............................. C12M 1/34; C09K 5/00; B01B 9/00
(52) U.S. Cl. .................. 435/287.2; 252/67; 252/537; 422/307
(58) Field of Search ............................ 435/6, 91.1, 91.2, 435/183, 287.2; 422/68.1, 234.5, 307; 252/67; 537; 536/23.1, 24.3

(56) References Cited

U.S. PATENT DOCUMENTS

| 4,683,195 | | 7/1987 | Mullis et al. ............................ 435/6 |
| 4,683,202 | | 7/1987 | Mullis et al. .......................... 435/91 |
| 4,829,324 | * | 5/1989 | Drake et al. ..................... 346/140 R |
| 5,091,328 | | 2/1992 | Miller ..................................... 437/52 |
| 5,587,128 | * | 12/1996 | Wilding et al. ....................... 422/50 |
| 5,922,591 | * | 7/1999 | Anderson et al. ................ 435/287.2 |

FOREIGN PATENT DOCUMENTS

2672301 * 8/1992 (FR) .

OTHER PUBLICATIONS

Marmur and Lane, Proc.Natl.Acad Sci., U.S.A. 46, 453 (1960).
Doty et al. Proc.Nat.Acad.Sci., U.S.A. 46, 461 (1960).
Hayashi et al., Proc.Nat.Acad.Sci., U.S.A. 50, 664 (1963).
Smith and Wilcox, J.Mol.Biol. 51, 379 (1970).
Southern, J.Mol.Biol. 98, 503 (1975).
Maxam and Gilbert, Proc. Natl. Acad Sci. USA 74:560 (1977).
Sanger et al., Proc. Natl. Acad Sci. USA 74:5463 (1977).
Graham et al., "Direct DNA sequencing using avian myeloblastosis virus and Moleney murine leukemia virus reverse transcriptase" Bethesda Res. Lab. Focus 8(2):4 (1986).
Sambrook, J. et al. Molecular Cloning, A Laboratory Manual, 2d Ed. Cold Spring Harbor Laboratory Press, New York, 13.7–13.9.
Hunkapiller, M.W. Curr. Op. Gen. Devl. 1:88–92 (1991).
Tabor et al., Proc. Natl. Acad. Sci. USA 84:4767 (1987).
Innis et al., Proc. Natl. Acad. Sci. USA 85:9436 (1988).
J. Pfahler et al., Sensors and Actuators, A21–A23, pp. 431–434 (1990).
H.T.G. Van Lintel et al., Sensors and Actuators 15:153–167 (1988).
Smits, "Piezoelectric Micropump with Three Valves Working Peristaltically," Sensors and Actuators A21–A23:203 (1990).
Mullis and Faloona, "Specific Synthesis of DNA in Vitro via a Polymerase–Catalyzed Chain Reaction," Meth. Enzym. 155:335 (1987).
Arnheim, "Polymerase Chain Reaction Strategy," Annu. Rev. Biochem. 61:131 (1992).
Nickerson et al., "Automated DNA diagnostics using an ELISA–based oligonucleotide ligation assay," Proc. Natl. Acad. Sci. USA 87:8923 (1990).
Gordon et al., "Capillary Electrophoresis," Science 27:224 (1988).
Lawrence Berkeley Lab Presentation, Park City, Utah (1993).
Turner, "New Dimensions in Capillary Electrophoresis Columns," LC–GC vol. 9 (1991).
Heller and Tullis, "Microelectrophoresis for the separation of DNA fragments," Electrophoresis 13:512 (1992).
Manz et al., "Planar chips technology for miniaturization and integration of separation techniques into monitoring systems Capillary electrophoresis on a chip," J. Chrom. 593:253 (1992).
Jorgenson and Lukacs, "High–Resolution Separations Based on Electrophoresis and Electroosmosis," J. Chrom. 218:209 (1981).
Chamberlain et al., "BRCA1 Maps Proximal to D17S579 on Chromosome 17q21 by Genetic Analysis," Am. J. Hum. Genet. 52:792 (1993).
Ansorge et al., "High–throughput automated DNA sequencing facility with fluorescent labels at the European Molecular Biology Laboratory," Electrophoresis 13:616 (1992).
Pentoney et al., "A single–fluor approach to DNA sequence determination using high performance capillary electrophoresis," Electrophoresis 13:467 (1992).
Daniel et al., French patent #2,672,301.
Tenan et al., "Friction in Capillary Systems," Journal of Applied Physics 53:6687 (1982).

(List continued on next page.)

Primary Examiner—Bradley L. Sisson
(74) Attorney, Agent, or Firm—Medlen & Carroll, LLP

(57) ABSTRACT

The movement and mixing of microdroplets through microchannels is described employing silicon-based microscale devices, comprising microdroplet transport channels, reaction regions, electrophoresis modules, and radiation detectors. The discrete droplets are differentially heated and propelled through etched channels. Electronic components are fabricated on the same substrate material, allowing sensors and controlling circuitry to be incorporated in the same device.

3 Claims, 7 Drawing Sheets

OTHER PUBLICATIONS

Dussan, "On the Spreading of Liquids on Solid Surfaces Static and Dynamic Contact Lines," Annual Review of Fluid Mechanics 11:371 (1979).

Probstein, "Physicochemical Hydrodynamics," (1989).

R.F. Service, "The Incredible Shrinking Laboratory," Science 268:26 (1995).

Presentation at Cold Spring Harbor (Aug. 31–Sep. 2, 1995).

R. Nowak, "Xeroxing DNA Analysis".

* cited by examiner $SiO_2$  Al  SiOx  SixNy

MICROSCALE DEVICES AND REACTIONS IN MICROSCALE DEVICES

This is a Divisional of application Ser. No. 08/529,293, filed on Sep. 15, 1995, issued as U.S. Pat. No. 6,057,149.

This invention was made with government support under HG01406, HG00209 and HG01044 awarded by NIH. The government has certain rights in the invention.

FIELD OF THE INVENTION

The present invention relates to microfabrication of microscale devices and reactions in microscale devices, and in particular, movement of biological samples in microdroplets through microchannels to initiate biological reactions.

BACKGROUND

The complexity and power of biological reactions has increased dramatically over the last thirty years. The initial observations of the "hybridization" process, i.e., the ability of two polymers of nucleic acid containing complementary sequences to find each other and anneal through base pairing interaction, by Marmur and Lane, Proc.Nat.Acad.Sci., U.S.A. 46, 453 (1960) and Doty, et al. Proc.Nat.Acad.Sci., U.S.A. 46, 461 (1960), have been followed by the refinement of this process into an essential tool of modern biology.

Initial hybridization studies, such as those performed by Hayashi, et al., Proc.Nat.Acad.Sci., U.S.A. 50, 664 (1963), were formed in solution. Further development led to the immobilization of the target DNA or RNA on solid supports. With the discovery of specific restriction endonucleases by Smith and Wilcox, J.Mol.Biol. 51, 379 (1970), it became possible to isolate discrete fragments of DNA. Utilization of immobilization techniques, such as those described by Southern, J.Mol.Biol. 98, 503 (1975), in combination with restriction enzymes, has allowed for the identification by hybridization of singly copy genes among a mass of fractionated, genomic DNA.

In 1977, two methods for DNA sequencing were reported. These were the chemical degradation method of Maxam and Gilbert (1977 Proc. Natl. Acad Sci. USA 74:560) and the enzymatic method of Sanger et al. (1977, Proc. Natl. Acad Sci. USA 74:5463). Both methods generate populations of radiolabeled oligonucleotides which begin at a fixed point and terminate randomly at a fixed residue or type of residue. These populations are resolved on polyacrylamide gels which allow the discrimination between oligonucleotides that differ in length by as little as one nucleotide.

The Maxam and Gilbert method utilizes a fragment of DNA radiolabeled at one end which is partially cleaved in five separate chemical reactions, each of which is specific for a particular base or type of base. The products of these chemical reactions are five populations of labelled molecules that extend from the labeled end to the site of chemical cleavage. This method has remained relatively unchanged since its initial development. This method works best for DNA sequences that lie less than 250 nucleotides from the labeled end.

In contrast, the Sanger method is capable of sequencing greater than 500 nucleotides in a single set of reactions. The Sanger method is an enzymatic reaction that utilizes chain-terminating dideoxynucleotides (ddNTPs). ddNTPs are chain-terminating because they lack a 3'-hydroxyl residue which prevents formation of a phosphodiester bond with the succeeding deoxyribonucleotide (dNTP). A small amount of one ddNTP is included with the four conventional dNTPs in a polymerization reaction. Polymerization or DNA synthesis is catalyzed by a DNA polymerase. There is competition between extension of the chain by incorporation of the conventional dNTPs and termination of the chain by incorporation of a ddNTP. A short oligonucleotide or primer is annealed to a template containing the DNA to be sequenced. The original protocols required single-stranded DNA templates. The use of double-stranded templates was reported later (Chen and Seeburg 1985). The primer provides a 3' hydroxyl group which allows the polymerization of a chain of DNA when a polymerase enzyme and dNTPs are provided.

The original version of the Sanger method utilized the Klenow fragment of E. coli DNA polymerase. This enzyme has the polymerization and 3' to 5' exonuclease activity of the unmodified polymerase but lacks 5' to 3' exonuclease activity. The Klenow fragment has several limitations when used for enzymatic sequencing. One limitations is the low processivity of the enzyme, which generates a high background of fragments that terminate by the random dissociation of the enzyme from the template rather than by the desired termination due to incorporation of a ddNTP. The low processivity also means that the enzyme cannot be used to sequence nucleotides that appear more than ~250 nucleotides from the 5' end of the primer. A second limitation is that Klenow cannot efficiently utilize templates which have homopolymer tracts or regions of high secondary structure. The problems caused by secondary structure in the template can be minimized by running the polymerization reaction at 55° C. (R. Gomer and R. Firtel, "Sequencing homopolymer regions." Bethesda Res. Lab. Focus 7:6 1985).

Improvements to the original Sanger method include the use of polymerases other than the Klenow fragment. Reverse transcriptase has been used to sequence templates that have homopolymeric tracts (S. Karanthanasis, "M13 DNA sequencing using reverse transcriptase" Bethesda Res. Lab. Focus 4(3):6 1982; Graham et al., "Direct DNA sequencing using avian myeloblastosis virus and Moleney murine leukemia virus reverse transcriptase" Bethesda Res. Lab. Focus 8(2):4 1986). Reverse transcriptase is somewhat better than the Klenow enzyme at utilizing templates containing homopolymer tracts.

The use of a modified T7 DNA polymerase (Sequenase™) was the most significant improvement to the Sanger method. See Sambrook, J. et al. Molecular Cloning, A Laboratory Manual, 2d Ed. Cold Spring Harbor Laboratory Press, New York, 13.7–13.9 and Hunkapiller, M. W. (1991) Curr. Op. Gen. Devl. 1:88–92. Sequenase™ is a chemically-modified T7 DNA polymerase has reduced 3' to 5' exonuclease activity (Tabor et al. 1987, Proc. Natl. Acad. Sci. USA 84:4767). Sequenase™ version 2.0 is a genetically engineered form of the T7 polymerase which completely lacks 3' to 5' exonuclease activity. Sequenase™ has a very high processivity and high rate of polymerization. It can efficiently incorporate nucleotide analogs such as dITP and 7-deaza-dGTP which are used to resolve regions of compression in sequencing gels. In regions of DNA containing a high G+C content, Hoogsteen bond formation can occur which leads to compressions in the DNA. These compressions result in aberrant migration patterns of oligonucleotide strands on sequencing gels. Because these base analogs pair weakly with conventional nucleotides, intrastrand secondary structures are alleviated. In contrast, Klenow does not incorporate these analogs as efficiently. The main limitation to the amount of DNA sequence that can be obtained from a single set of chain-termination reactions using Sequenase™ is the resolving power of polyacrylamide gels, not the properties of the enzyme.

The use of Taq DNA polymerase is a more recent addition to the improvements of the Sanger method (Innis et al 1988, Proc. Natl. Acad. Sci. USA 85:9436). Taq polymerase is a thermostable enzyme which works efficiently at 70–75° C. The ability to catalyze DNA synthesis at elevated temperature makes Taq polymerase useful for sequencing templates which have extensive secondary structures at 37° C. (the standard temperature used for Klenow and Sequenase™ reactions). Taq polymerase, like Sequenase™, has a high degree of processivity and like Sequenase 2.0, it lacks 3' to 5' nuclease activity.

Methods were also developed for examining single base changes without direct sequencing. These methods allow for the "scanning" of DNA fragments for the presence of mutations or other sequence variation. For example, if a mutation of interest happens to fall within a restriction recognition sequence, a change in the pattern of digestion can be used as a diagnostic tool (e.g., restriction fragment length polymorphism [RFLP] analysis).

With the development of these complex and powerful biological techniques, an ambitious project has been undertaken. This project, called the Human Genome Project (HGP), involves the complete characterization of the archetypal human genome sequence which comprises $3\times10^9$ DNA nucleotide base pairs. An implicit goal of the project is the recognition that all humans are greater than 99% identical at the DNA sequence level. The differences between people, however, provide the information most relevant to individual health care, including potential estimates of the risk of disease or the response to a specific medical treatment. Upon completion of the HGP, a continuing effort of the human genetics research community will be the examination of differences within populations and of individual variants from the defined archetype. While the 15-year effort of the HGP represents a defined quantity of DNA data acquisition, the future demand for DNA information is tied to individual genetic variation and is, therefore, unlimited.

Current DNA genotyping technologies are adequate for the detailed analysis of samples that range in number from hundreds to thousands per year. Genotyping projects on the order of millions of assays, however, are beyond the capabilities of today's laboratories because of the current inefficiencies in (i) liquid handling of reagent and DNA template solutions, (ii) measurement of solution volumes, (iii) mixing of reagent and template, (iv) controlled thermal reaction of the mixed solutions, (v) sample loading onto an electrophoresis gel, and (vi) DNA product detection on size-separating gels. What is needed is methodology that allows for a high-volume of biological reactions without these existing inefficiencies.

SUMMARY OF THE INVENTION

The present invention relates to microfabrication of microscale devices and reactions in microscale devices, and in particular, movement of biological samples in microdroplets through microchannels to initiate biological reactions. The present invention contemplates microscale devices, comprising microdroplet transport channels, reaction regions (e.g. chambers), electrophoresis modules, and radiation detectors. In a preferred embodiment, these elements are microfabricated from silicon and glass substrates. The various components are linked (i.e., in liquid communication) using a surface-tension-gradient mechanism in which discrete droplets are differentially heated and propelled through etched channels. Electronic components are fabricated on the same substrate material, allowing sensors and controlling circuitry to be incorporated in the same device. Since all of the components are made using conventional photolithographic techniques, multi-component devices can be readily assembled into complex, integrated systems.

It is not intended that the present invention be limited by the nature of the reactions carried out in the microscale device. Reactions include, but are not limited to, chemical and biological reactions. Biological reactions include, but are not limited to sequencing, restriction enzyme digests, RFLP, nucleic acid amplification, and gel electrophoresis. It is also not intended that the invention be limited by the particular purpose for carrying out the biological reactions. In one medical diagnostic application, it may be desirable to differentiate between a heterozygotic and homozygotic target and, in the latter case, specifying which homozygote is present. Where a given genetic locus might code for allele A or allele a, the assay allows for the differentiation of an AA from an Aa from an aa pair of alleles. In another medical diagnostic application, it may be desirable to simply detect the presence or absence of specific allelic variants of pathogens in a clinical sample. For example, different species or subspecies of bacteria may have different susceptibilities to antibiotics; rapid identification of the specific species or subspecies present aids diagnosis and allows initiation of appropriate treatment.

The present invention contemplates a method for moving microdroplets, comprising: (a) providing a liquid microdroplet disposed within a microdroplet transport channel etched in silicon, said channel in liquid communication with a reaction region via said transport channel and separated from a microdroplet flow-directing means by a liquid barrier; and (b) conveying said microdroplet in said transport channel to said reaction region via said microdroplet flow-directing means. It is intended that the present invention be limited by the particular nature of the microdroplet flow-directing means. In one embodiment, it comprises a series of aluminum heating elements arrayed along said transport channel and the microdroplets are conveyed by differential heating of the microdroplet by the heating elements.

It has been found empirically that the methods and devices of the present invention can be used with success when, prior to the conveying described above the transport channel (or channels) is treated with a hydrophilicity-enhancing compound. It is not intended that the invention be limited by exactly when the treatment takes place. Indeed, there is some flexibility because of the long-life characteristics of some enhancing compounds.

Again, it has been found empirically that there is a need for a liquid barrier between the liquid in the channels and the electronics of the silicon chip. A preferred barrier comprises a first silicon oxide layer, a silicon nitride-layer, and a second silicon oxide layer.

The present invention further contemplates a method for merging microdroplets comprising: (a) providing first and second liquid microdroplets, a liquid microdroplet delivering means, and a device, said device comprising: i) a housing comprised of silicon, ii) first and second microdroplet transport channels etched in said silicon and connecting to form a third transport channel containing a reaction region, iii) a microdroplet receiving means in liquid communication with said reaction region via said transport channels, and iv) microdroplet flow-directing means arrayed along said first, second and third transport channels; (b) delivering said first liquid microdroplet via said microdroplet delivering means to said first transport channel; (c)

delivering said second liquid microdroplet via said microdroplet delivering means to said second transport channel; and (d) conveying said microdroplets in said transport channels to said reaction region in said third transport channel via said microdroplet flow-directing means, thereby merging said first and second microdroplets to create a merged microdroplet.

In one embodiment, said first microdroplet comprises nucleic acid and said second microdroplet comprises a nuclease capable of acting on said nucleic acid. In this embodiment, it is desirable to enhance the mixing within the merged microdroplet. This can be achieved a number of ways. In one embodiment for mixing, after the conveying of step (d), the flow direction is reversed. It is not intended that the present invention be limited by the nature or number of reversals. If the flow direction of said merged microdroplet is reversed even a single time, this process increases the mixing of the reactants.

The present invention contemplates a variety of silicon-based, microdroplet transport channel-containing devices. In one embodiment, the device comprises: i) a housing comprised of silicon, ii) a microdroplet transport channel etched in said silicon, iii) a microdroplet receiving means in liquid communication with a reaction region via said transport channels, and iv) a liquid barrier disposed between said transport channels and a microdroplet flow-directing means. In one embodiment, the device is assembled in two parts. First, the channels are etched in any number of configurations. Secondly, this piece is bonded with a silicon-based chip containing the electronics. This allows for both customization (in the first piece) and standardization (in the second piece).

Definitions

The following definitions are provided for the terms used herein:

"Biological reactions" means reactions involving biomolecules such as enzymes (e.g., polymerases, nucleases, etc.) and nucleic acids (both RNA and DNA). Biological samples are those containing biomolecules, such proteins, lipids, nucleic acids. The sample may be from a microorganism (e.g., bacterial culture) or from an animal, including humans (e.g. blood, urine, etc.). Alternatively, the sample may have been subject to purification (e.g. extraction) or other treatment. Biological reactions require some degree of biocompatability with the device. That is to say, the reactions ideally should not be substantially inhibited by the characteristics or nature of the device components.

"Chemical reactions" means reactions involving chemical reactants, such as inorganic compounds.

"Channels" are pathways through a medium (e.g., silicon) that allow for movement of liquids and gasses. Channels thus can connect other components, i.e., keep components "in liquid communication." "Microdroplet transport channels" are channels configured (in microns) so as to accommodate "microdroplets." While it is not intended that the present invention be limited by precise dimensions of the channels or precise volumes for microdroplets, illustrative ranges for channels and microdroplets are as follows: the channels can be between 0.35 and 50 $\mu$m in depth (preferably 20 $\mu$m) and between 50 and 1000 $\mu$m in width (preferably 500 $\mu$m), and the volume of the microdroplets can range (calculated from their lengths) between approximately one (1) and (100) nanoliters (more typically between ten and fifty).

"Conveying" means "causing to be moved through" as in the case where a microdroplet is conveyed through a transport channel to a particular point, such as a reaction region. Conveying can be accomplished via flow-directing means.

"Flow-directing means" is any means by which movement of a microdroplet in a particular direction is achieved. A preferred directing means employs a surface-tension-gradient mechanism in which discrete droplets are differentially heated and propelled through etched channels.

"Hydrophilicity-enhancing compounds" are those compounds or preparations that enhance the hydrophilicity of a component, such as the hydrophilicity of a transport channel. The definition is functional, rather than structural. For example, Rain-X™ anti-fog is a commercially available reagent containing glycols and siloxanes in ethyl alcohol. However, the fact that it renders a glass or silicon surface more hydrophilic is more important than the reagent's particular formula.

"Initiating a reaction" means causing a reaction to take place. Reactions can be initiated by any means (e.g., heat, wavelengths of light, addition of a catalyst, etc.)

"Liquid barrier" or "moisture barrier" is any structure or treatment process on existing structures that prevents short circuits and/or damage to electronic elements (e.g., prevents the destruction of the aluminum heating elements). In one embodiment of the present invention, the liquid barrier comprises a first silicon oxide layer, a silicon nitride layer, and a second silicon oxide layer.

"Merging" is distinct from "mixing." When a first and second microdroplet is merged to create a merged microdroplet, the liquid may or may not be mixed. Moreover, the degree of mixing in a merged microdroplet can be enhanced by a variety of techniques contemplated by the present invention, including by not limited to reversing the flow direction of the merged microdroplet.

"Nucleic Acid Amplification" involves increasing the concentration of nucleic acid, and in particular, the concentration of a particular piece of nucleic acid. A preferred technique is known as the "polymerase chain reaction." Mullis, et al., U.S. Pat. Nos. 4,683,195 and 4,683,202, hereby incorporated by reference, describe a method for increasing the concentration of a segment of target sequence in a mixture of genomic DNA without cloning or purification. This process for amplifying the target sequence consists of introducing a molar excess of two oligonucleotide primers to the DNA mixture containing the desired target sequence. The two primers are complementary to their respective strands of the double-stranded sequence. The mixture is denatured and then allowed to hybridize. Following hybridization, the primers are extended with polymerase so as to form complementary strands. The steps of denaturation, hybridization, and polymerase extension can be repeated as often as needed to obtain are relatively high concentration of a segment of the desired target sequence. The length of the segment of the desired target sequence is determined by the relative positions of the primers with respect to each other, and therefore, this length is a controllable parameter. By virtue of the repeating aspect of the process, the method is referred to by the inventors as the "Polymerase Chain Reaction" (hereinafter PCR). Because the desired segment of the target sequence become the dominant sequences (in terms of concentration) in the mixture, they are said to be "PCR-amplified."

DESCRIPTION OF THE INVENTION

The present invention relates to microfabrication and biological reactions in microfabricated devices, and in particular, movement and mixing of biological samples in microdroplets through microchannels. The description of the invention involves I) design of microscale devices (comprising microdroplet transport channels, reaction chambers, electrophoresis ports, and radiation detectors) using silicon and glass substrates, II) movement of discrete microdroplets using a surface-tension-gradient mechanism in which discrete microdroplets are differentially heated and propelled through etched channels, and III) mixing of biological samples for reactions.

I. Design Of MicroScale Devices

Although there are many formats, materials, and size scales for constructing integrated fluidic systems, the present invention contemplates silicon microfabricated devices as a cost-effective solution. Silicon is the material used for the construction of computing microprocessors and its fabrication technologies have developed at an unprecedented pace over the past 30 years. While this technology was initially applied to making microelectronic devices, the same techniques are currently being used for micromechanical systems.

Continuous flow liquid transport has been described using a microfluidic device developed with silicon. See J. Pfahler et al., Sensors and Actuators, A21–A23 (1990), pp. 431–434. Pumps have also been described, using external forces to create flow, based on micromachining of silicon. See H. T. G. Van Lintel et al., Sensors and Actuators 15:153–167 (1988). By contrast, the present invention employs discrete droplet transport in silicon (i.e., in contrast to continuous flow) using internal forces (i.e., in contrast to the use of external forces created by pumps).

As a mechanical building material, silicon has well-known fabrication characteristics. The economic attraction of silicon devices is that their associated micromachining technologies are, essentially, photographic reproduction techniques. In these processes, transparent templates or masks containing opaque designs are used to photodefine objects on the surface of the silicon substrate. The patterns on the templates are generated with computer-aided design programs and can delineate structures with line-widths of less than one micron. Once a template is generated, it can be used almost indefinitely to produce identical replicate structures. Consequently, even extremely complex micromachines can be reproduced in mass quantities and at low incremental unit cost—provided that all of the components are compatible with the silicon micromachining process. While other substrates, such as glass or quartz, can use photolithographic methods to construct microfabricated analysis devices, only silicon gives the added advantage of allowing a large variety of electronic components to be fabricated within the same structure.

Figure 1:
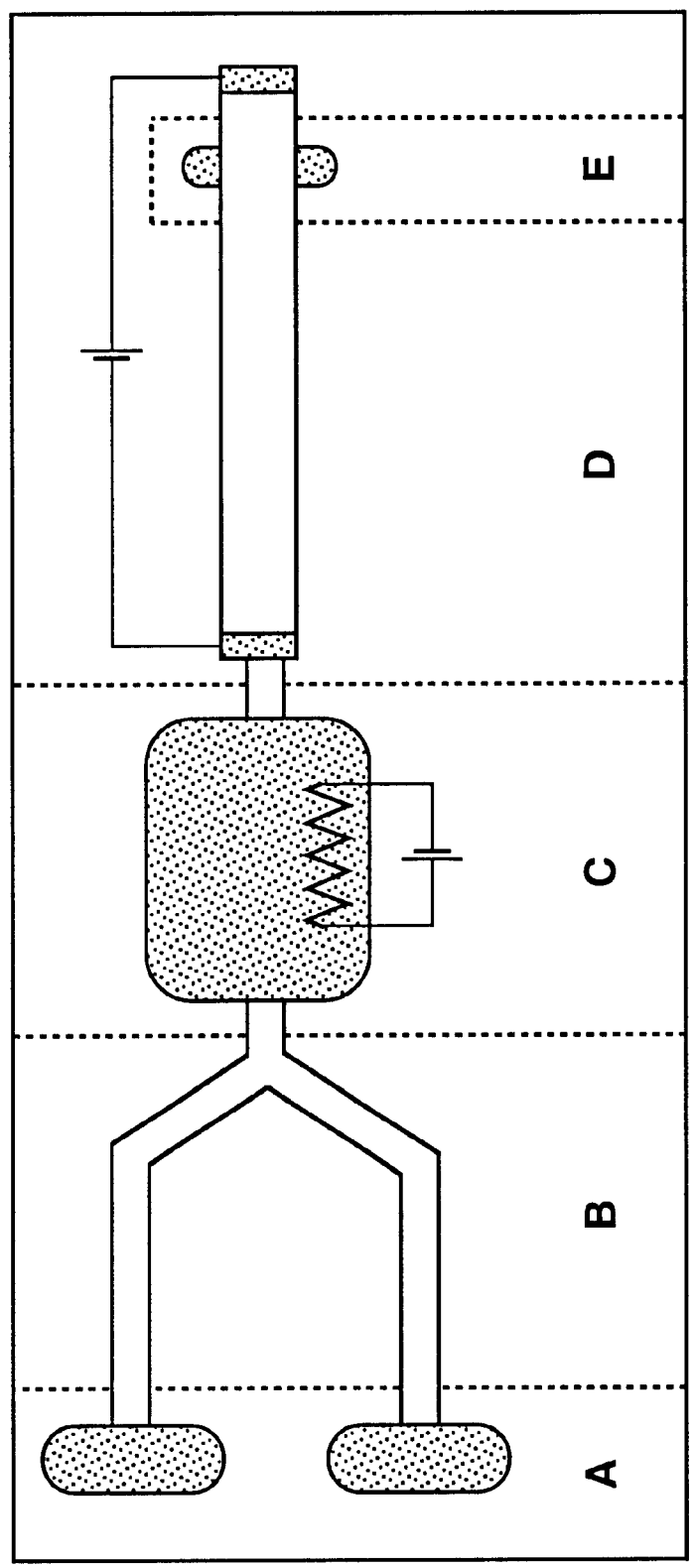
FIG. 1 is a schematic of an integrated analysis system of the present invention.

In one embodiment, the present invention contemplates silicon micromachined components in an integrated analysis system, including the elements identified schematically in FIG. 1. In this proposed format, sample and reagent are injected into the device through entry ports (A) and they are transported as discrete droplets through channels (B) to a reaction chamber, such as a thermally controlled reactor where mixing and reactions (e.g., restriction enzyme digestion or nucleic acid amplification) occur (C). The biochemical products are then moved by the same method to an electrophoresis module (D) where migration data is collected by a detector (E) and transmitted to a recording instrument (not shown). Importantly, the fluidic and electronic components are designed to be fully compatible in function and construction with the biological reactions and reagents.

In silicon micromachining, a simple technique to form closed channels involves etching an open trough on the surface of a substrate and then bonding a second, unetched substrate over the open channel. There are a wide variety of isotropic and anisotropic etch reagents, either liquid or gaseous, that can produce channels with well-defined side walls and uniform etch depths. Since the paths of the channels are defined by the photo-process mask, the complexity of channel patterns on the device is virtually unlimited. Controlled etching can also produce sample entry holes that pass completely through the substrate, resulting in entry ports on the outside surface of the device connected to channel structures.

Figure 2:
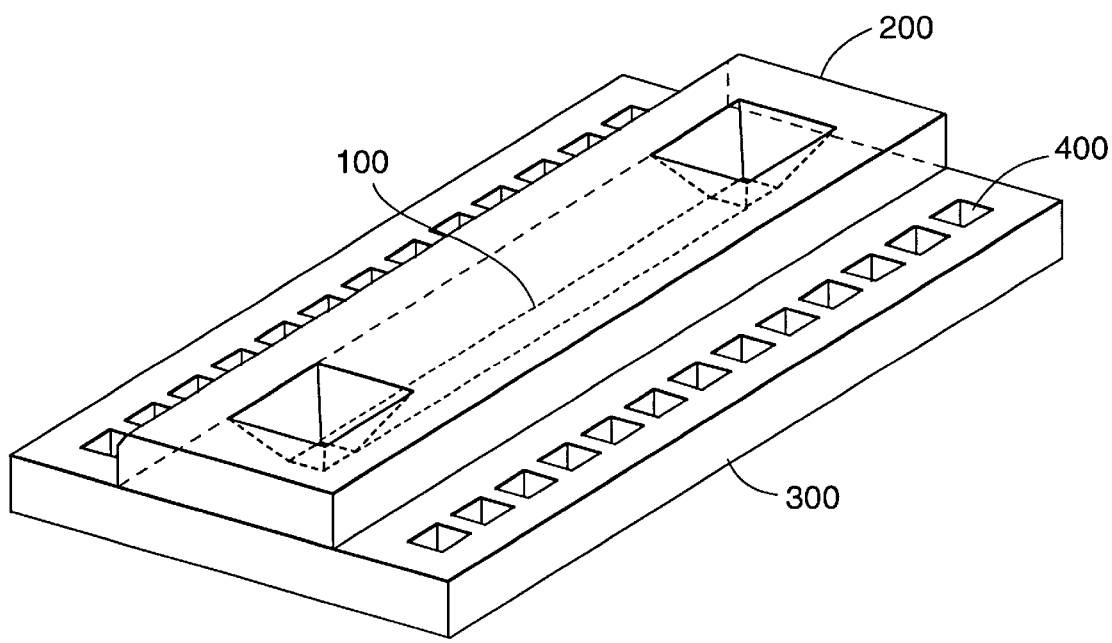
FIG. 2 shows a two-part approach to construction of a silicon device of the present invention.

FIG. 2 shows a two-part approach to construction. Microchannels (100) are made in the silicon substrate (200) and the structure is bonded to a glass substrate (300). The two-part channel construction technique requires alignment and bonding processes but is amenable to a variety of substrates and channel profiles. In other words, for manufacturing purposes, the two-part approach allows for customizing one piece (i.e., the silicon with channels and reaction formats) and bonding with a standardized (non-customized) second piece, e.g., containing standard electrical pads (400).

II. Movement Of Discrete MicroDroplets

Figure 3:
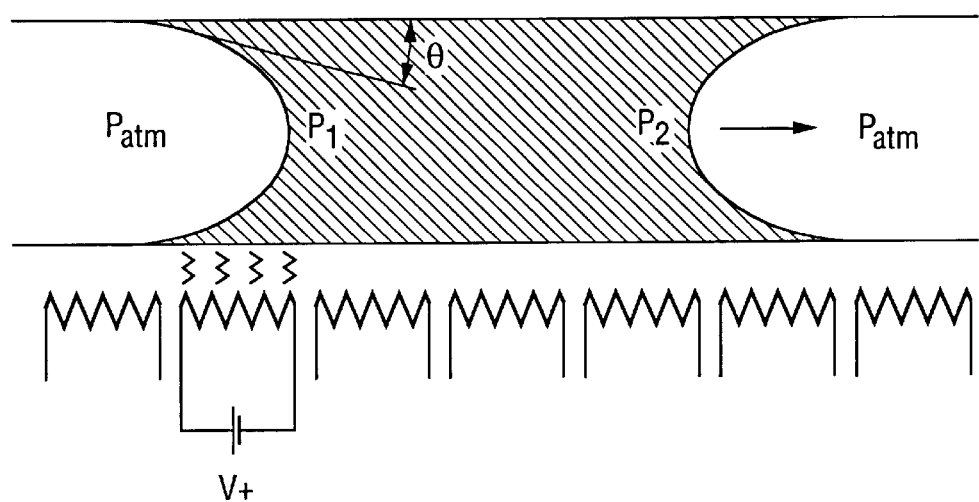
FIG. 3 is a schematic showing the principle of thermally-induced liquid microdroplet motion in a closed channel.

The present invention describes the controlled movement of liquid samples in discrete droplets in silicon. Discrete droplet transport involves a system using enclosed channels or tubes to transport the liquid to the desired locations (FIG. 1, B). Within the channels, discrete liquid reagent microdroplets can be injected, measured, and moved between the biochemical analysis components. Discrete droplet movement has three advantages. First, each sample droplet is separated from all others so that the risk of contamination is reduced. Second, in a uniform channel, the volume of each sample can be determined by merely measuring the droplet length. Third, the motion of these droplets can be accomplished with simple heating (i.e., using internal forces and no moving parts). Movement is performed using thermal gradients to change the interfacial tension at the front or back of the droplets and, thus, generate pressure differences across the droplet (FIG. 3). For example, a droplet in a hydrophilic channel can be propelled forward by heating the back interface. The local increase in temperature reduces the surface tension on the back surface of the droplet and, therefore, decreases the interfacial pressure difference. The decreased pressure difference corresponds to an increase in the local internal pressure on that end of the droplet ($P_1$ increases). The two droplet interfaces are no longer in equilibrium, with $P_1$ greater than $P_2$, and the pressure difference propels the droplet forward.

That is to say, forward motion can be maintained by continuing to heat the droplet at the rear surface with successive heaters along the channel, while heating the front surface can be used to reverse the motion of the droplet. Applying a voltage to the wire beneath the channel generates heat under the edge of the droplet. Heating the left interface increases the internal pressure on that end of the droplet and forces the entire droplet to the right. The pressure on the interior of the droplet can be calculated knowing the atmospheric pressure, $P_{atm}$, the surface tension, $\sigma$, and the dimensions of the channel. For a circular cross-section, the interior pressure, $P_i$, is given by $P_i = P_{atm} - (4\sigma \cos \theta)/d$ where d is the diameter of the channel and $\theta$ is the contact angle. Since $\sigma$ is a function of temperature ($\sigma = \sigma_o(1-bT)$ where $\sigma_o$ and b are positive constants and T is the temperature), increasing the temperature on the left end of the droplet decreases the surface tension and, therefore, increases the internal pressure on that end. The pressure difference between the two ends then pushes the droplet towards the direction of lower pressure (i.e., towards the right). The aqueous droplet shown is in a hydrophilic channel ($0 < \theta < 90$); for a hydrophobic channel ($90 < \theta < 180$), heating the right edge would make the droplet move to the right.

Contact angle hysteresis (the contact angle on the advancing edge of the droplet is larger than the contact angle on the retreating edge) requires a minimum temperature difference before movement will occur. The velocity of the droplet after motion begins can be approximated using the equation $v = \Delta EPd^2/32 \mu L$ where $\Delta EP$ is the pressure difference, $\mu$ is the viscosity of the solution, and L is the length of the droplet. The present invention contemplates temperature differences of greater than thirty (30) degrees Centigrade to create movement Experiments using temperature sensors arrayed along the entire channel indicate that a differential of approximately 40° C. across the droplet is sufficient to provide motion. In these experiments, the channel cross-section was 20 $\mu$m×500 $\mu$m, and the volume of each of these droplets can be calculated from their lengths and is approximately 100 nanoliters for a 1 cm long droplet.

III. Mixing Biological Samples In Reactions

Figure 4A:
FIG. 4A shows a selected frame of a videotape wherein two microdroplets are at their starting locations in the branches of the Y-channel.
Figure 4B:
FIG. 4B shows movement by heating the left interface of both microdroplets.
Figure 4C:
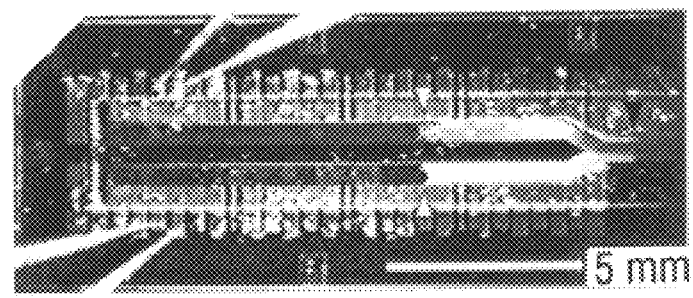
FIG. 4C shows the microdroplets at the intersection.

Droplet motion (described generally above) is contemplated as one step in a pathway. The other steps typically involve sample mixing and a controlled reaction. For example, the integral heaters arrayed along the entire surface of the channel used for droplet motion also allow for a region of a channel to be used as a thermal reaction chamber. For sample mixing prior to the reaction, a Y-channel device is contemplated (FIG. 4A). In such a device, a fist droplet containing a first sample (e.g., nucleic acid) is moved along one channel of the Y-channel device, and a second droplet containing a second sample (e.g., a restriction digest enzyme in digestion buffer) is moved along the other channel of the Y-channel device (FIGS. 4B and 4C)

Following sample merging (FIG. 4D), there is the concern that the combined samples have not been properly mixed. That is to say, if two similar microdroplets enter the single channel in laminar flow at the same flow rate, they will form an axially uniform droplet but will not be mixed width-wise. Width-mixing can be accomplished in a number of ways.

First, there is simple diffusion, although, for large DNA molecules, the characteristic time for this mixing could be on the order of several hours or more. Circulation patterns generated inside the droplets during movement and heating significantly reduce this time. In this regard, the present invention contemplates maintaining the mixture as a heated mixture (e.g., maintaining the temperature at 65° C. for 10 minutes) using the integral heaters and temperature sensors.

Second, the present invention contemplates mixing by reversing the flow direction of the mixture over a relatively short distance in the channel. While a variety of reverse flow approaches are possible, one or two direction changes over a distance comprising approximately two droplet lengths has been found to be adequate.

Finally, there is the mixing approach wherein the mixture is moved against or over physical obstacles. For example, the mixture can be either "crashed" back against merge point of the Y-channel or simply moved over deliberate imperfections in the channel (i.e., "roller coaster" mixing).

Successful mixing, of course, can be confirmed by characterization of the product(s) from the reaction. Where product is detected, mixing has been at least partially successful. The present invention contemplates, in one embodiment, using electrophoresis to confirm product formation.

DESCRIPTION OF PREFERRED EMBODIMENTS

The description of the preferred embodiments involves: I) microfabrication techniques for manufacture of silicon-based devices; II) channel treatment for optimum flow and reproducibility; and III) component design (particularly the electrophoresis module and the radiation detectors).

I. Microfabrication Of Silicon-Based Devices

As noted previously, silicon has well-known fabrication characteristics and associated photographic reproduction techniques. The principal modern method for fabricating semiconductor integrated circuits is the so-called planar process. The planar process relies on the unique characteristics of silicon and comprises a complex sequence of manufacturing steps involving deposition, oxidation, photolithography, diffusion and/or ion implantation, and metallization, to fabricate a "layered" integrated circuit device in a silicon substrate. See e.g., W. Miller, U.S. Pat. No. 5,091,328, hereby incorporated by reference.

For example, oxidation of a crystalline silicon substrate results in the formation of a layer of silicon dioxide on the substrate surface. Photolithography can then be used to selectively pattern and etch the silicon dioxide layer to expose a portion of the underlying substrate. These openings in the silicon dioxide layer allow for the introduction ("doping") of ions ("dopant") into defined areas of the underlying silicon. The silicon dioxide acts as a mask; that is, doping only occurs where there are openings. Careful control of the doping process and of the type of dopant allows for the creation of localized areas of different electrical resistivity in the silicon. The particular placement of acceptor ion-doped (positive free hole, "p") regions and donor ion-doped (negative free electron, "n") regions in large part defines the interrelated design of the transistors, resistors, capacitors and other circuit elements on the silicon wafer. Electrical interconnection and contact to the, various p or n regions that make up the integrated circuit is made by a deposition of a thin film of conductive material, usually aluminum or polysilicon, thereby finalizing the design of the integrated circuit.

Of course, the particular fabrication process and sequence used will depend on the desired characteristics of the device. Today, one can choose from among a wide variety of devices and circuits to implement a desired digital or analog logic feature.

In a preferred embodiment, channels were prepared on 500 $\mu$m thick glass wafers (Dow Corning 7740) using standard aqueous-based etch procedures. The initial glass surface was cleaned and received two layers of electron beam evaporated metal (20 nm chromium followed by 50 nm gold). Photoresist Microposit 1813 (Shipley Co.) was applied 4000 rpm, 30 seconds; patterned using glass mask 1 and developed. The metal layers were etched in chromium etchant (Cr-14, Cyantek Inc.) and gold etchant (Gold Etchant TFA, Transene Co.) until the pattern was clearly visible on the glass surface. The accessible glass was then etched in a solution of hydrofluoric acid and water (1:1, v/v). Etch rates were estimated using test wafers, with the final etch typically giving channel depths of 20 to 30 $\mu$m. For each wafer, the depth of the finished channel was determined using a surface profilometer. The final stripping (PRS-2000, J. T. Baker) removed both the remaining photoresist material and the overlying metal.

In one embodiment, channels etched on glass in the above-described manner, were bonded to the heater-element wafer in a two-part construction approach using optical adhesive (SK-9 Lens Bond, Sumers Laboratories, Fort Washington, Pa). The bond was cured under an ultraviolet light source (365 nm) for 12 to 24 hours.

Figure 5A:
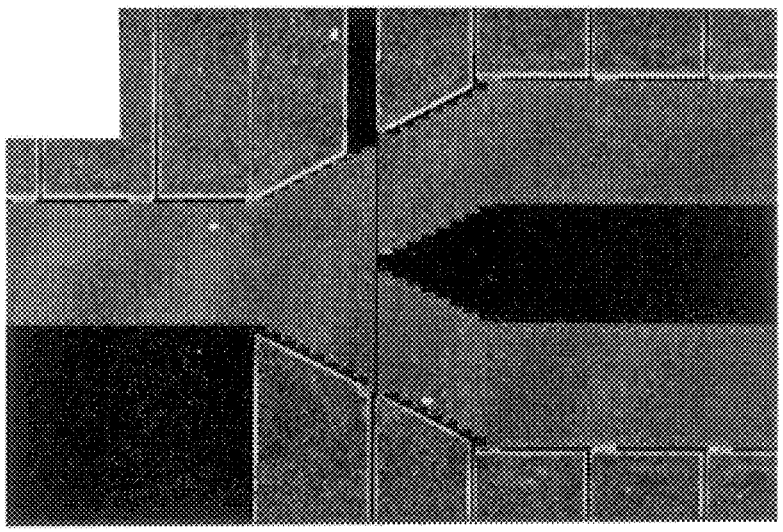
FIG. 5A is a photomicrograph of inlay-process heater elements on the surface of a silicon wafer.
Figure 5B:
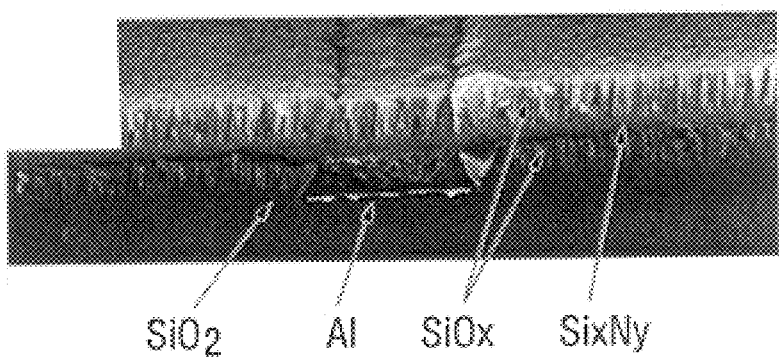
FIG. 5B is a scanning electron micrograph (SEM) of an inlay-process heater wire in cross section (the arrows indicate the deposited aluminum, silicon dioxide, and silicon nitride layers).

Initial device design by the present inventors involved single layers of silicon. However, experience showed these to be inadequate to prevent short circuiting due to (necessary) liquid microdroplets within the channels (see experiments described below). The preferred design involves a triple layer of oxides. Such a preferred device capable of moving and mixing nanoliter droplets was constructed by bonding a planar silicon substrate to channels etched in a glass cover. A series of metal heaters was inlaid on the silicon substrate as two parallel lanes merging into a single lane (a "Y"-shape) (FIG. 5A). The heating elements were formed by first coating the wafer with a 1.0 $\mu$m layer of thermal silicon dioxide Next, 0.35 $\mu$m deep, 5 $\mu$m wide grooves were reactive-ion etched (RIE) into the silicon dioxide following the pattern set in an overlying photoresist. Aluminum was deposited (0.35 $\mu$m) across the entire wafer using electron beam evaporation and the metal layer was "lifted-off" from all surfaces having intact photoresist using a stripping solution. The metal inlay process gives a relatively planar surface and provides a uniform base for deposition of a solution-impermeable barrier layer. The barrier layer is made by a sequence of three plasma-enhanced chemical vapor depositions (PECVD): 1.0 $\mu$m silicon oxide ($SiO_x$), 0.25 $\mu$m silicon nitride ($Si_xN_y$), and 1.0 $\mu$m silicon oxide ($SiO_x$) (FIG. 5B). Some heating elements were also used as resistive temperature sensors.

Heater elements were fabricated as follows. Silicon wafer (p-type, 18–22 ½-cm, (100), boron concentration Å $10^{15}$ $cm^{-3}$) was used as a substrate for growth of $SiO_2$ thermal oxide (1 $\mu$m); photoresist (AZ-5214-E, Hoescht-Celanese) was applied and spun at 3000 rpm, 30 seconds. The resist was patterned (metal 1) and developed. Reactive ion etch (RIE, PlasmaTherm, Inc.) was performed to 0.35 $\mu$m depth into the $SiO_2$ layer at the following conditions: $CHF_3$, 15 sccm (standard cubic centimeters per minute); $CF_4$, 15 sccm; 4 mTorr; DC bias voltage of 200 V, 100 W, 20 minutes. The etch depth was measured by profilometer and 0.35 $\mu$m metallic aluminum was electron beam deposited. The resist and overlying metal was lifted off by development using Microposit 1112A remover in solution (Shipley Co.). The barrier layers consist of sequentially deposited 1 $\mu$m $SiO_x$, 0.25 $\mu$m $Si_xN_y$, and 1 $\mu$m $SiO_x$ using plasma-enhanced chemical vapor deposition (PECVD). RIE was used to etch contact holes to the metal layer using a second mask ($CHF_3$, 15 sccm; $CF_4$, 15 sccm; 4 mTorr; and DC bias voltage of 200 V, 100 W, 120 minutes).

Figure 5C:
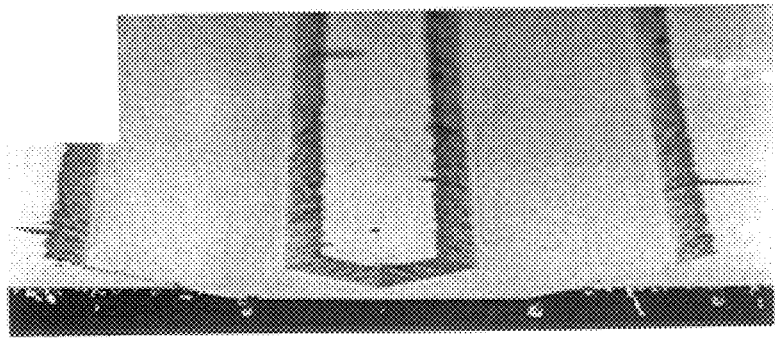
FIG. 5C is a SEM of a channel formed on glass using a wet-etch process, shown in cross section with the etched face of the wafer immediately adjacent to the intersection of two channels.

As shown in FIG. 5, the elements are arrayed as two parallel lanes, each 500 $\mu$m wide, merging into one lane. The individual heaters consist of paired aluminum wires (5 $\mu$m) winding across the 500 $\mu$m wide region. The broad metal areas on either side of the elements are bonding locations for connection to external circuitry. The width of the aluminum element is 5 $\mu$m. The channel in FIG. 5C has identical width and design configurations as the heating element lanes in FIG. 5A, and is uniformly etched 500 $\mu$m wide and approximately 20 $\mu$m deep.

The heating-element wafer was bonded to a glass wafer containing etched channels with the same "Y" format. An aqueous chemical etch of concentrated hydrofluoric acid was used to produce channels with defined side walls and uniform depth. The etched channels are defined by a chromium/gold mask and are 500 $\mu$m wide and approximately 20 $\mu$m deep (FIG. 5C). The complementary silicon heater and glass channel wafers were aligned and then bonded with adhesive to form the finished device.

Each heating element used as a temperature sensor is preferably first calibrated by measurement of electrical resistance at 22° C. and 65° C. under constant voltage; intermediate temperatures are estimated by linear interpolation.

II. Channel Treatment

Prior to performing microdroplet motion and biological reactions, the channels are preferably treated by washing with base, acid, buffer, water and a hydrophilicity-enhancing compound, followed by a relatively high concentration solution of non-specific protein. In a preferred embodiment, the channels are washed with approximately 100 $\mu$l each of the following solutions in series: 0.1N NaOH; 0.1N HCl; 10 mM Tris-HCl (pH 8.0), deionized $H_2O$, Rain-X Anti-Fog (a hydrophilicity-enhancing compound commercially available from Unelko Corp., Scottsdale, Ariz.), and 500 $\mu g/\mu l$ bovine serum albumin (non-specific protein commercially available in restriction enzyme grade from GIBCO-BRL). The wafer was placed on a stereoscope stage (Olympus SZ1145), and the contact pads for the heating elements were connected to a regulated power supply. Heating occurred by passing approximately 30 volts through the element in short pulses and observing the movement rate of the droplets. A detectable reduction in droplet volume from evaporation was noted in each experiment, usually of less than 30%. Droplet movement was recorded with a Hamamatsu video camera on videotape.

III. Component Design

The present invention contemplates one or more gel electrophoresis modules as a component of the microscale device. Theoretical and empirical research has indicated that reducing the thickness of the electrophoresis channel leads to improved resolution. Thinner gels dissipate heat more readily and allow higher voltages to be used, with concomitant improvements in separation. The position and width of the electrophoresis detector are also critical to the ultimate resolution of the electrophoresis system. A micromachined electronic detector, such as a photodiode, placed in the underlying silicon substrate can be less than one micron from the gel matrix and can have a width of 5 microns or less. Since the gel length required for the resolution of two migrating bands is proportional to the resolution of the detector, the incorporation of micron-width electronic detectors can reduce the total gel length required for standard genotyping by at least an order of magnitude.

Figure 6A:
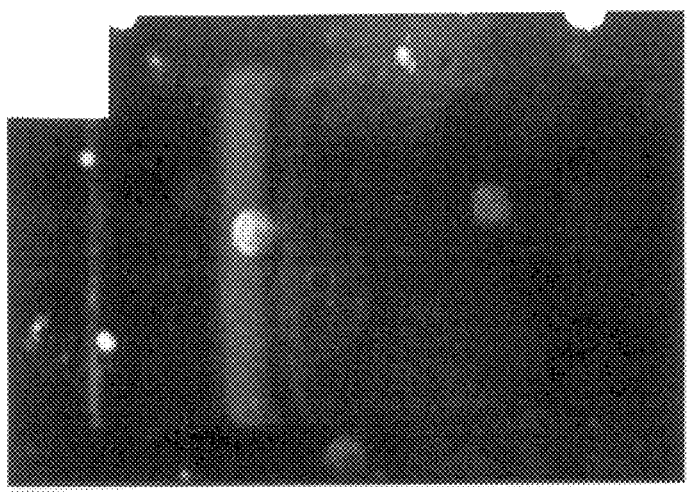
FIG. 6A is a photomicrograph of polyacrylamide gel electrophoresis in a wide etched-glass channel.

To demonstrate that standard gel electrophoresis can operate in micron-diameter channels, modules were fabricated using etched glass channels identical to FIG. 4B and fluorescent-labeled DNA (YOYO intercalating dye). Polyacrylamide gel electrophoresis of a complex DNA mixture is shown in FIG. 6A in a channel 500 $\mu$m wide and 20 $\mu$m deep. The electrophoresis was performed with the positive electrode to the right and the DNA sample applied at the left. The white vertical line is the gel-to-buffer interface. The DNA sample (BluescriptKS digested with MspI) is labeled with intercalating UV-fluorescent dye (YOYO-1) and is visualized under incandescent light. Separation of the component bands is clearly visible less than 300 $\mu$m from the buffer reservoir-to-gel interface. The high resolution of the detector (in this case, a microscope) allowed the use of an unusually short gel, resolving several closely eluting bands.

Figure 4D:
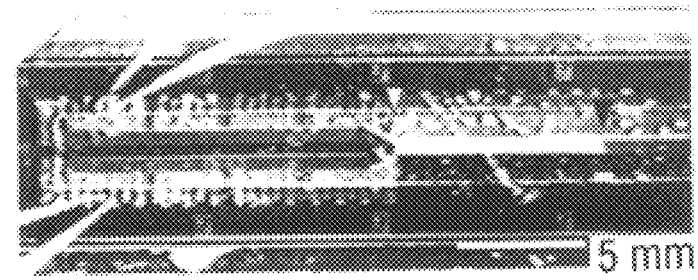
FIG. 4D shows the merging of the microdroplets to form the combined microdroplet. The open arrowheads in the figure indicate the rear meniscus and the filled arrowheads the leading meniscus for each microdroplet.

The present invention contemplates an electrophoresis unit that integrates a micromachined channel and an electronic DNA detector. The channel is constructed using a sacrificial etch process on a single silicon wafer rather than the bonded surface-etch method described earlier. In the sacrificial etch technique, the channel configuration is patterned by depositing on the wafer surface an etch-sensitive material (phosphosilicate glass, $SiO_2.P_x$) with a thickness equivalent to the desired channel height. A triple-layer overlay of plasma-enhanced chemical vapor deposited silicon nitride, undoped polycrystalline silicon, and silicon nitride ($Si_xN_y$/polySi/$Si_xN_y$) completely covers the sacrificial material with the exception of small access holes on the top or sides. A selective liquid etch removes the sacrificial layer material, but not the overlay or the underlying substrate. The sacrificial etch technique results in a complete channel being formed directly on the substrate containing the electronic components (FIGS. 4C and 4D). The 3 $\mu$m deep channel has two buffer reservoirs on either end with integral phosphorus-doped polycrystalline silicon electrodes. The channel height formed by this technique (~3 $\mu$m) is considerably smaller than the height of the bonded structures due to the limitations of the sacrificial layer deposition and the strength of the overlying layer. Note that, for these channel dimensions, liquid drops would have volumes on the order of picoliters.

Figure 6B:
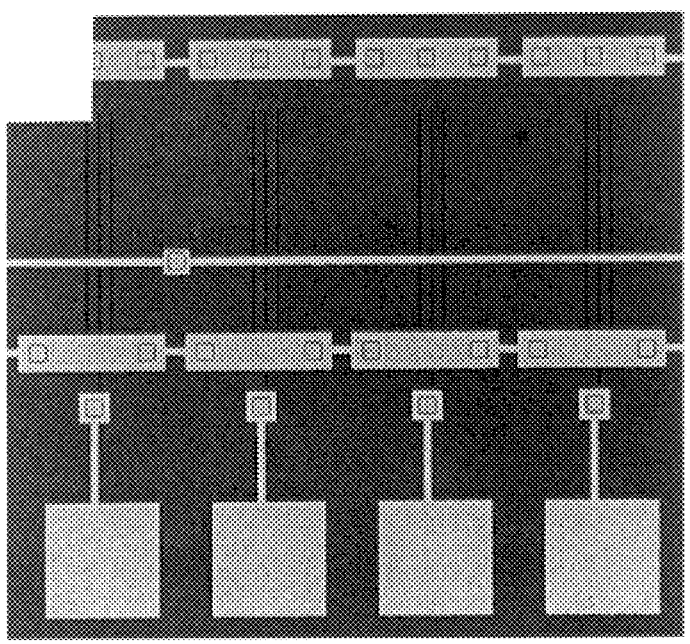
FIG. 6B is a photomicrograph of a set of four doped-diffusion diode radiation detector elements fabricated on a silicon wafer.

FIG. 6B is photomicrograph of a set of four doped-diffusion diode radiation detector elements fabricated on a silicon wafer. For each element, the three parallel dark lines define the diffusion regions of the central the detector flanked by the guard ring shielding electrodes. The diffusion regions are approximately 300 $\mu$m long and 4 $\mu$m wide.

A radiation detector, consisting of a 10 $\mu$m wide "p-n"-type diode with a 5 $\mu$m wide guard ring around the outer edge, is fashioned directly into the silicon substrate underneath the channel. In this implementation, an integral radiation detector was chosen because of (i) high sensitivity (a single decay event), (ii) small aperture dimensions, and (iii) well-know fabrication and response characteristics. On this electrophoresis system, a 1 cm long, 3 $\mu$m thick gel is able to perform as separation on a 80 and a 300 base-pair fragment of DNA. It should be noted that this diode, although currently configured for high-energy beta particle detection, can also operate as a photon detector. With proper wavelength filters and light sources, detection of fluorescence emission may be accommodated with a similar device.

Radiation detectors were prepared as follows. A 200 ½-cm, <100>, float zone, boron-doped, p-type silicon wafer was used as a substrate. Diffused layers of phosphorus ($5\times10^{14}$ $cm^{-2}$) and boron ($1\times10^{15}$ $cm^{-2}$) were ion-implanted onto the sample in lithographically-defined regions; thermal silicon oxide was grown (0.2 $\mu$m at 900° C.) over the wafer; and contact holes were etched to the diffusion layer using buffered hydrofluoric acid solution (5:1). A 3.3 $\mu$m layer of Microposit 1400-37 photoresist was patterned to define the metal pads; 50 nm chromium followed by 400 nm gold was evaporated over the resist; and the metallization lifted off the regions retaining the resist. A layer of Microposit 1813 photoresist was applied across the wafer and baked for 110° C. for 30 minutes to form an aqueous solution barrier. Radioactive phosphorus ($^{32}P$) decay events could be detected using a sample of labeled DNA in PCR reaction buffer placed on the photoresist layer. The detector was connected to a charge-sensitive preamplifier (EV-Products 550A), followed by a linear shaping amplifier and a standard oscilloscope.

Figure 6C:
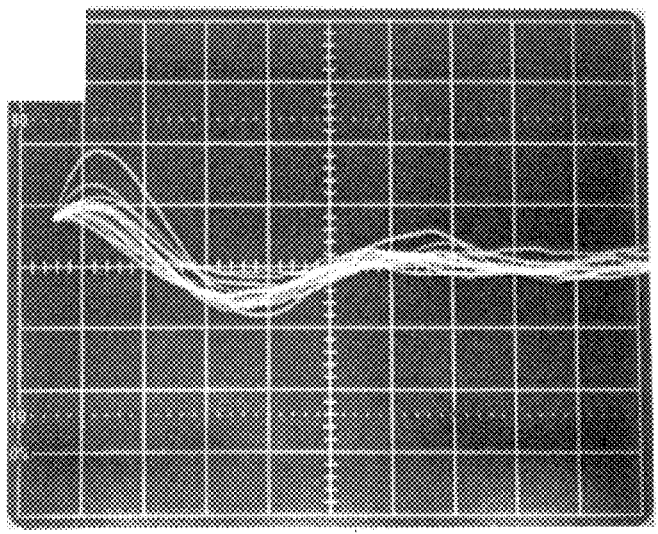
FIG. 6C is an oscilloscope trace of output from the radiation detector showing individual decay events from $^{32}$P-labeled DNA.

FIG. 6C shows an oscilloscope trace of output from the radiation detector showing individual decay events from $^{32}$P-labeled DNA. The aqueous DNA sample was placed directly on the detector and sampled for 30 seconds. The screen is displaying a vertical scale of 0.5V/division and horizontal scale of 20 $\mu$sec/division.

Experimental

The following examples serve to illustrate certain preferred embodiments and aspects of the present invention and are not to be construed as limiting the scope thereof.

In the experimental disclosure which follows, the following abbreviations apply: eq (equivalents); M (Molar); $\mu$M (micromolar); N (Normal); mol (moles); mmol (millimoles); $\mu$mol (micromoles); nmol (nanomoles); gm (grams); mg (milligrams); $\mu$g (micrograms); L (liters); ml (milliliters); $\mu$l (microliters); cm (centimeters); mm (millimeters); $\mu$m (micrometers); nm (nanometers); ° C. (degrees Centigrade); Ci (Curies); MW (molecular weight); OD (optical density); EDTA (ethylenediamine-tetracetic acid); PAGE (polyacrylamide gel electrophoresis); UV (ultraviolet); V (volts); W (watts); mA (milliamps); bp (base pair); CPM (counts per minute).

EXAMPLE 1

This example describes approaches to the problem of forming a moisture barrier over electrical elements of the microscale device. Initial prototypes employed 5000 angstroms of aluminum and covered it with PECVD $SiO_x$. Upon testing, it was determined that the liquids were penetrating this later and destroying the aluminum heating elements.

Without clear evidence what was causing this problem, it was hypothesized that the step height of the aluminum was causing cracks in the passivation layer (the oxide). In order to alleviate the cracking problem, a layer of $Si_xN_y$ was tried between two layers of $SiO_x$, with the thought that the additional thickness would overcome the cracking caused by the step height. It did not.

As a follow-up approach, a thinner layer (500 angstroms) of aluminum was tried. This gave 1/10th the step height of the original prototype devices. On top of this aluminum, a triple layer of $SiO_x$, $Si_xN_y$, and $SiO_x$ was employed. Moreover, the process for making the $Si_xN_y$ layer was changed to one which would give a more dense layer. This appeared to solve the problem. However, the thinner layer of aluminum created a higher resistance which was not acceptable. It was determined that one needed a way to generate thicker layers of aluminum for lower resistance, yet keep the surface relatively smooth (planar). An etch back process was used (now called "the inlay process") to accomplish the task. By etching back into a layer of $SiO_x$ depositing aluminum in the resulting cavity, then stripping the resist mask, a surface was obtained with a step height low enough to prevent cracking of the passivation layers.

It was also discovered that the metal bonding pads were not adhering well to the initial PECVD $SiO_x$ layer. To overcome the problem, the process was modified by using a wet thermal $SiO_2$ layer.

EXAMPLE 2

This example describes approaches to enhancing droplet motion by surface treatment. In this regard, the principle of using surface tension to cause droplets to move may be applied to either hydrophilic or hydrophobic surfaces. Glass, for instance, is naturally hydrophilic with a near zero contact angle with water. Because the oxide coating of the present invention is made principally of the same material as glass, it was expected that the devices would also exhibit near zero angles. It was discovered, however, that the actual construction materials had contact angles far from zero, thus enhancing the effects of contact angle hysteresis (discussed in greater detail in Example 3). For instance, water gave a contact angle (static) of ~42° on polyamide, ~41° on $SiO_2$ (major component of most glasses), ~62° on silicone spray. To enhance the surface effectiveness, several treatment processes for both hydrophilic and hydrophobic surfaces were tried, as described below.

To improve the hydrophilicity of a surface, several cleaning procedures were tried. It has been reported that surface contamination and/or roughness can reduce the hydrophilicity of surfaces. Therefore, a high concentration chromic acid cleaning, a high concentration sulfuric acid cleaning, a baking procedure (to 600° C. for 8 hrs. to burn off contaminates), and surface coatings were tried. The acid cleaning procedures were not as effective as the baking procedure; however, neither proved to be compatible with the devices since the concentrated acids would attack the aluminum pads and the high temperature could peal the aluminum (melting pt. ~660° C.) or break the adhesive bond between the heater chip and the channel.

Rain-X antifog (commercially available) as a treatment was observed to work. This is a surface treatment which makes surfaces hydrophilic. Although, the resulting surfaces may not be 0°, by using this coating the entire surface gets treated giving a uniform surface for the droplet. Experimentally, it was found that Rain-X antifog treatments greatly enhanced droplet motion experiments using heat. Another such treatment which was tested but which did not work was a material called SilWet. This material is used in the agriculture industry for enhancing the wetting of plants with agricultural sprays.

To obtain hydrophobic surfaces, the present inventors tried coating capillaries with Rain-X and silane treatments. Neither of these gave angles much greater than 90°, therefore, would not work with this mechanism. These treatments would have to have given angles ~180° to be useful for hydrophobic studies of motion. Eventually, it was discovered that one could apply a teflon coating that was sufficiently hydrophobic to possibly warrant future tests.

EXAMPLE 3

This example describes approaches to droplet motion by heat treatment. As noted previously (above), the contact angle on the advancing end of a liquid droplet in motion (known as the advancing contact angle) is greater that the that on the receding end (receding contact angle). In the case of a hydrophilic surface—such as water on glass—this tends to create a back pressure countering attempts at forward motion by heating the back side of a droplet. This is best shown by a simple model describing laminar flow through a channel.

Average Flow Through a Circular Channel:

$<v> = -\Delta P^*[R^2/(8\mu L]$ where:

$\Delta$=value at back–value at front end of droplet $\Delta P=(1/R)^*(\Delta G)$=pressure difference between droplet ends $\Delta G$=change in surface tension between the ends of the droplet.

R=channel radius

L=droplet length $\mu$=viscosity

Also, for water, $\Delta G=$-constant$^*\Delta T$, where temperature increases lower the surface tension of most liquids (constant=0.16 dyn/cm for water).

Therefore:

$<v>=-(\Delta G)^*(1/R)^*[R^2/(8\mu L)]=[-0.16^*\Delta T^* R/(8\mu L)]$ where:

$\Delta T = T_{back} - T_{front}$ giving:

$<v>=[0.16^*R/(8\mu L)]^*(T_{back}-T_{front})$.

This expression indicates that any heating on the back end of the droplet (if the front remains at a lower temperature) will cause the liquid droplet to move. This was not the case experimentally, however. By way of studies using glass capillaries, it was found that there was a minimum temperature difference required to move the droplet. This effect is believed to be the result of contact angle hysteresis (CAH). In CAH, the advancing contact angle is greater than the receding contact angle resulting in a sort of back pressure which must be overcome to achieve droplet movement. CAH occurs when the interface is placed in motion (dynamic angles). To account for this effect, it was included in a steady-state (1D) model for flow. For instance, if the advancing angle is 36° and the receding angle is 29° (with the front of the droplet being 25° C.), then the back of the droplet would need to be heated to ~60° C. for a 1 mm long droplet in a 20 $\mu$m high channel. This is just one example situation.

It was discovered experimentally, however, that the channel dimension and fluid parameters (other than surface tension) do not affect whether or not the droplet will move. They do determine the magnitude of motion (if it occurs). What does determine whether motion will occur or not is the following inequality:

$$G_{front}/G_{back} > (R_{front}/R_{back})*(\cos \beta_{back}/\cos \beta_{front})$$

where: β=contact angle.

The present calculations suggest that a ~35° C. difference between the front and back of a droplet should be sufficient to initiate droplet motion in a system with advancing angles of 36° and receding angles of 29° in a 20 μm high channel. Experimental testing of actual devices however, showed that the front of the droplet heats relatively quickly thus reducing the temperature difference needed for movement between the front and the back of the droplet. This effect required us to use higher voltages to obtain droplet motion. Voltages typically in the range of ~30° Volts were found to be required to obtain motion. Further experiments showed that the resulting temperature difference was ~40° C. between the front and back of the droplet thus corroborating the initial determination of the requirements.

Discrete droplet motion in a micromachined channel structure using thermal gradients is demonstrated in the videorecorded images of FIG. 4. The device consists of a series of aluminum heaters inlaid on a planar silicon dioxide substrate (similar to the structure shown in FIG. 2) and bonded by glue to a wet-etched glass channel (20 μm depth, 500 μm width). Liquid samples were manually loaded into the two channels on the left using a micropipette. Heating the left interface of each droplet propels it toward the intersection of the channels. At the intersection, the droplets meet and join to form a single larger droplet. Note that, since the channel cross-section is 20 μm×500 μm, the volume of each of these droplets can be calculated from their lengths and is approximately 50 nanoliters.

The heaters along the entire surface of the channel shown in FIG. 4 allow it to be used as a thermal reaction chamber in addition to a droplet-motion device. The upper droplet in the figure contains a DNA sample, while the lower contains a restriction digest enzyme (TaqI) and digestion buffer. Following sample merging, the combined droplet was maintained at 65° C. for 30 minutes using the integral heaters and temperature sensors. The completed enzymatic reaction was confirmed by expressing the droplet from the right end of the channel and loading it onto a capillary gel electrophoresis system with a laser-induced fluorescence detector. The chromatogram produced by the silicon-device sample was similar to chromatograms generated from DNA digests runs in a standard polypropylene microreaction vessel (not shown).

EXAMPLE 4

This example describes various approaches for bonding channels to the substrate which contains circuitry for heating and temperature sensing of the device of the present invention (see discussion of two-part construction, above). First attempts involved Polyamide; regular polyamide was unsatisfactory in that it was found the two pieces would not stick together.

Follow-up attempts involved a photo-definable Polyamide. This produced a sticky surface, but would not give a perfect seal along the channel. It was discovered that the solvents released during the final baking process were causing pockets in the polyamide layer. An adhesion layer was needed which would seal by 'curing' and not release solvents.

Several different epoxies and glues were investigated, as listed below.

| Adhesive | Form | Dries | Texture | Comments |
|---|---|---|---|---|
| 1. Dymax UV Glue | Gel | Clear | Rubbery | Cures on UV exposure. |
| 2. Carter's Rubber Cement | Goo | Yellow/Clear | Rubbery | Dries quickly and stringy when thinned. |
| 3. Borden's Krazy Glue | Liquid | Clear | Hard | Thin, dries on first contact. |
| 4. UHU Bond-All | Gel/Goo | Clear | Hard | Dries quickly and stringy when thin. |
| 5. Dennison Permanent Glue Stick | Paste | Clear | Hard | Will not flow on applying. |
| 6. Elmer's Glue-All (Borden) | Thick Liquid | White | Hard | Slow drying. |
| 7. Liquid Nails | Thin Paste | Wood-like | Hard | Thick, dries quickly when thinned. |
| 8. Devcon 5-Minute Epoxy | Gel | Yellow/Clear | Hard | Thick, cures on about 5 min. |
| 9. Scotch Double-Stick Tape | Tape | Clear | Rubbery | Tape. |
| 10. Dow Corning High Vacuum Grease | Thick Gel | Frosty | Soft | Seals but does not bond. |
| 11. Nujol Mineral Oil (Perkin Elmer) | Liquid | Clear | Runny | Neither seals (doesn't spread on glass) nor bonds. |
| 12. Household Goop | Gel/Goo | Clear | Rubbery | Contact cement which dries stringy. |
| 13. Permatex Weather Strip Cement | Gel/Goo | Yellow/Clear | Rubbery | Dries quickly and stringy when thinned. |
| 14. Thick Gel Super Glue | Gel | Clear | Hard | Does not cure on contact but does quickly. |
| 15. DAP Weldwood Contact Cement | Goo | Orange/Clear | Rubbery | Contact cement which gets stringy when thinned. |
| 16. Scotch (3M) Photo Mount Spray Adhesive | Thin Goo | Yellow/Clear | Rubbery | Spray. 'Gooey' but not stringy. |
| 17. Silicone Resin (spray) Lacquer (GC Electronics) | Liquid | Clear | Smooth | Spray. Dries to thin, clear, and sealed coating. |

A preferred glue was a UV cured glue, although the process of applying the UV glue is tedious and requires some practice to avoid putting the glue in places where it does not belong, e.g., in the channels.

Hydroxide bonding and screen printing of bonding substances was also attempted. Another option was glass tape, but the high temperatures required to melt the tape appeared to be too high for the present devices.

EXAMPLE 5

This example describes a nucleic acid amplification reaction on a silicon-based substrate. The established DNA biochemistry steps for PCR occur within physiological conditions of ionic strength, temperature, and pH. Thus, the reaction chamber components have design limitations in that there must be compatibility with the DNA, enzymes and other reagents in solution.

Figure 7:
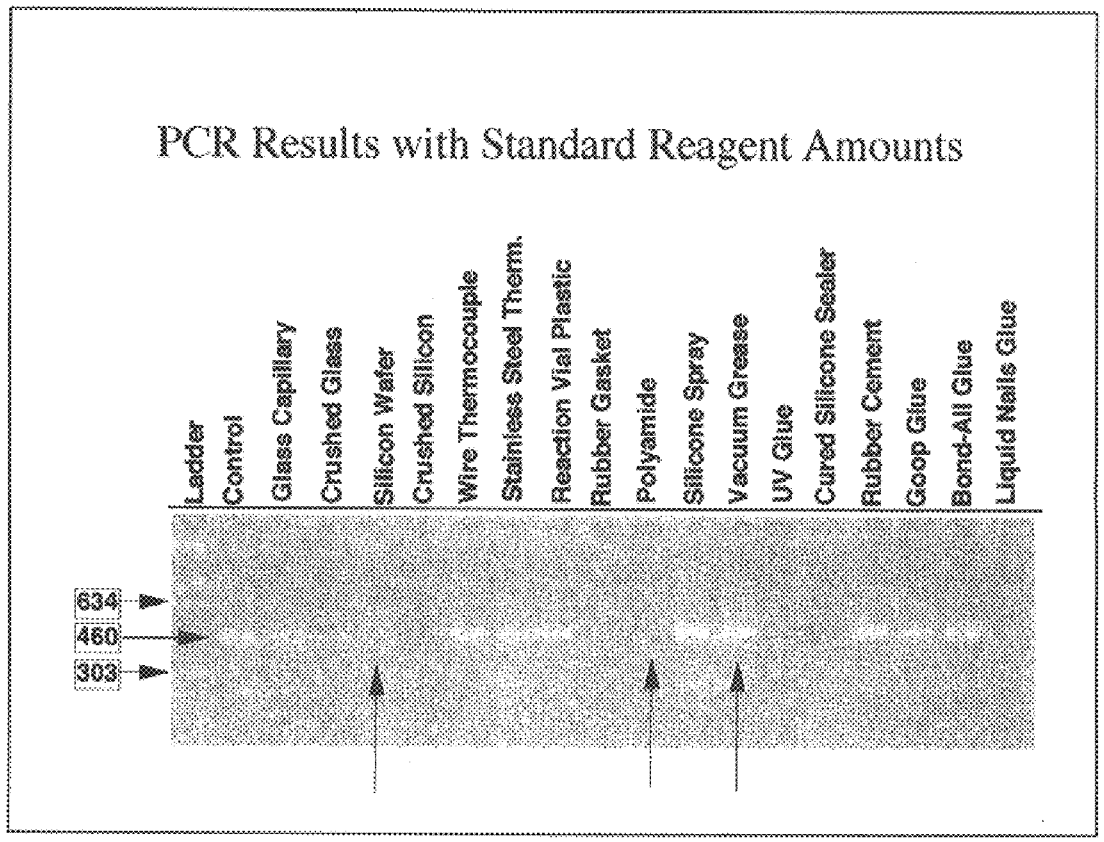
FIG. 7 is a photo of gel electrophoresis of PCR reactions wherein potentially inhibiting components were added directly to the PCR.

To assess biocompatability, components were added to a standard PCR reaction. The results (see FIG. 7) indicated that crystalline silicon may not be the ideal material for biological compatibility. Given these results, it may be desirable to modify the surface of the micromachined silicon substrate with adsorbed surface agents, covalently bonded polymers, or a deposited silicon oxide layer.

To form a biologically compatible heating element, the present inventors began by coating a standard silicon wafer with a 0.5 $\mu$m layer of silicon dioxide. Next, a 0.3 $\mu$m deep, 500 $\mu$m wide channel was etched into the silicon oxide and gold or aluminum was deposited (0.3 $\mu$m thick). This inlay process results in a relatively planar surface (FIG. 2A) and provides a base for deposition of a water-impermeable layer. The impermeable layer is made by a sequence of three plasma enhanced vapor depositions: silicon oxide ($SiO_x$), silicon nitride ($Si_xN_y$), and silicon oxide ($SiO_x$). Since the materials are deposited from the vapor phase the precise stoichiometries are not known. A thin metal heater design was used for this device rather than the doped-silicon resistive heaters previously demonstrated for micromachined PCR reaction chambers, since the narrow metal inlay allows viewing of the liquid sample through a transparent underlying substrate, such as glass or quartz. Also, the use of several independent heating elements permits a small number to operate as highly accurate resistive temperature sensors, while the majority of elements are functioning as heaters.

A device fabricated with metal resistive heaters and oxide/nitride/oxide coating was tested for biological compatibility and temperature control by using PCR amplification of a known DNA template sample. The reaction was carried out on the planar device using twenty microliters of PCR reaction mix covered with mineral oil to prevent evaporation. The reaction mixture was cycled through a standard 35-cycle PCR temperature cycling regime using the integral temperature sensors linked to a programmable controller. Since the reaction volume was significantly larger than intended for the original heater design, a polypropylene ring was cemented to the heater surface to serve as a sample containment chamber. In all test cases, the presence of amplified reaction products indicated that the silicon dioxide surface and the heater design did not inhibit the reaction. Parallel amplification experiments performed on a commercial PCR thermocycler gave similar results. A series of PCR compatibility tests indicated that the reaction on the device is very sensitive to controller settings and to the final surface material in contact with the sample (not shown).

From the above it should be evident that the present invention can be adapted for high-volume projects, such as genotyping. The microdroplet transport avoids the current inefficiencies in liquid handling and mixing of reagents. Moreover, the devices are not limited by the nature of the reactions, including biological reactions.

We claim:

1. A device comprising:
    i) a housing comprised of silicon,
    ii) a microdroplet transport channel etched in said silicon,
    iii) a microdroplet receiving means in liquid communication with a reaction region via said transport channels, and
    iv) a liquid barrier disposed between said transport channels and a microdroplet flow-directing means wherein said liquid barrier comprises a first silicon oxide layer, a silicon nitride layer, and a second silicon oxide layer.

2. The device of claim 1 wherein said microdroplet flow-directing means comprises a series of heating elements arrayed along said transport channels.

3. The device of claim 1 wherein said channel has been treated with a hydrophilicity-enhancing compound.

* * * * *

UNITED STATES PATENT AND TRADEMARK OFFICE
CERTIFICATE OF CORRECTION

PATENT NO. : 6,271,021 B1  
APPLICATION NO. : 09/271963  
DATED : August 7, 2001  
INVENTOR(S) : Burns et al.

It is certified that error appears in the above-identified patent and that said Letters Patent is hereby corrected as shown below:

On Title Page (75) Inventors should read:

Mark A. Burns; Carlos H. Mastrangelo; Timothy S. Sammarco, Francis P. Man; James R. Webster; Brian N. Johnson; Bradley Foerster; Darren Jones; Yakeitha Fields; Adam Keiser; David T. Burke; all of Ann Arbor, MI (US)

Signed and Sealed this

First Day of August, 2006

JON W. DUDAS  
*Director of the United States Patent and Trademark Office*